(12) United States Patent
Qing et al.

(10) Patent No.: US 8,265,889 B2
(45) Date of Patent: Sep. 11, 2012

(54) INTEGRATED CIRCUIT SYSTEM FOR CONTROLLING STRUCTURAL HEALTH MONITORING PROCESSES AND APPLICATIONS THEREFOR

(75) Inventors: Xinlin Qing, Cupertino, CA (US); Chang Zhang, Santa Clara, CA (US); Irene Li, Stanford, CA (US); Fu-kuo Chang, Stanford, CA (US); Hung Chi Chung, Santa Clara, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 392 days.

(21) Appl. No.: 12/536,429

(22) Filed: Aug. 5, 2009

(65) Prior Publication Data
US 2011/0035167 A1  Feb. 10, 2011

(51) Int. Cl.
*G01R 31/307* (2006.01)
(52) U.S. Cl. .............. 702/58; 702/36; 702/39; 702/183; 73/579; 73/583; 73/628; 29/600; 29/825
(58) Field of Classification Search .............. 702/34, 702/35, 36, 39, 58; 760/760, 767, 772, 587, 760/588, 789, 801, 802, 803, 584; 73/628, 73/579, 768, 583, 799, 862.046, 862.041, 73/760, 767, 772, 587, 588, 789, 801, 802, 73/803, 584; 29/600, 825, 953; 370/201, 370/241
See application file for complete search history.

(56) References Cited

U.S. PATENT DOCUMENTS

| | | | | |
|---|---|---|---|---|
| 6,006,163 A * | 12/1999 | Lichtenwalner et al. | ....... | 702/36 |
| 7,034,660 B2 * | 4/2006 | Watters et al. | ............. | 340/10.41 |
| 7,286,964 B2 * | 10/2007 | Kim | .............................. | 702/183 |
| 7,322,244 B2 * | 1/2008 | Kim | ................................ | 73/587 |
| 7,366,627 B2 * | 4/2008 | Gordon et al. | ................ | 702/105 |
| 7,458,266 B2 * | 12/2008 | Beard et al. | ...................... | 73/579 |
| 7,596,078 B2 * | 9/2009 | Beard et al. | .................... | 370/201 |
| 7,881,881 B2 * | 2/2011 | Giurgiutiu et al. | .............. | 702/39 |
| 7,986,218 B2 * | 7/2011 | Watters et al. | ............. | 340/10.41 |
| 2002/0154029 A1 * | 10/2002 | Watters et al. | ........... | 340/870.07 |
| 2005/0075846 A1 * | 4/2005 | Kim | ...................................... | 703/1 |
| 2006/0170535 A1 * | 8/2006 | Watters et al. | ............. | 340/10.41 |
| 2009/0043516 A1 * | 2/2009 | Liu et al. | .......................... | 702/35 |
| 2009/0326834 A1 * | 12/2009 | Sundaresan et al. | ............ | 702/34 |
| 2010/0132469 A1 * | 6/2010 | Giurgiutiu et al. | ............... | 73/628 |

* cited by examiner

*Primary Examiner* — Carol Tsai
(74) *Attorney, Agent, or Firm* — Innovation Counsel LLP (57) ABSTRACT

A structural health monitoring system using ASICs for signal transmission, reception, and analysis. Incorporating structural health monitoring functionality into one or more ASICs provides a durable yet small, lightweight, low cost, and portable system that can be deployed and operated in field conditions. Such systems provide significant advantages, especially in applications such as armor structures.

16 Claims, 10 Drawing Sheets

INTEGRATED CIRCUIT SYSTEM FOR CONTROLLING STRUCTURAL HEALTH MONITORING PROCESSES AND APPLICATIONS THEREFOR

BRIEF DESCRIPTION

This invention relates generally to structural health monitoring. More specifically, this invention relates to an integrated circuit system for controlling structural health monitoring processes, and applications therefor.

BACKGROUND

Many current structural health monitoring techniques are not well suited for use outside of a controlled laboratory environment. For example, traditional nondestructive inspection techniques, such as ultrasound and X-radiography, require controlled conditions and highly trained technicians. Techniques such as these are thus often inconvenient and, when the cost of setting up/maintaining such laboratory conditions is included, expensive. Accordingly, it is desirable to develop structural health monitoring devices and techniques that are suitable for use outside the laboratory. In particular, it is desirable to develop structural health monitoring systems capable of use in field conditions, where light-weight, small, and cost-effective systems are advantageous.

SUMMARY

The invention can be implemented in a number of ways, including as a structural health monitoring system.

In one embodiment, a structural health monitoring system comprises a structure, and at least one integrated circuit. The at least one integrated circuit is configured to transmit interrogating signals to a plurality of actuators coupled to the structure, to receive sensor signals from a plurality of sensors coupled to the structure, and to determine a health of the structure according to a comparison of the received sensor signals to baseline signals. The interrogating signals correspond to stress waves propagated through the structure so as to query the structure, the sensor signals correspond to stress waves detected by the plurality of sensors, the baseline signals correspond to a baseline state of the structure, and one or more integrated circuits of the at least one integrated circuit are coupled to the structure.

In a further embodiment, a structural health monitoring system comprises a first integrated circuit and a second integrated circuit. The first integrated circuit comprises a processing block receiving sensor signals from sensors affixed to a structure, comparing the sensor signals to baseline signals, generating results data from the comparing, and generating interrogation signals initiating transmission of interrogating signals for interrogating the structure. The first integrated circuit also comprises a waveform generation block receiving the interrogation signals from the processing block and generating corresponding ones of the interrogating signals. The second integrated circuit comprises a signal conditioning block receiving the sensor signals, conditioning the sensor signals, and transmitting the conditioned sensor signals for receiving by the processing block of the first integrated circuit. The second integrated circuit also comprises a multiplexer block routing the interrogating signals to predetermined actuators affixed to the structure.

Other aspects and advantages of the invention will become apparent from the following detailed description taken in conjunction with the accompanying drawings which illustrate, by way of example, the principles of the invention.

BRIEF DESCRIPTION OF THE DRAWINGS

For a better understanding of the invention, reference should be made to the following detailed description taken in conjunction with the accompanying drawings, in which.

Like reference numerals refer to corresponding parts throughout the drawings.

DETAILED DESCRIPTION OF EMBODIMENTS

In one embodiment, the invention relates to a structural health monitoring system using ASICs for signal transmission, reception, and analysis. In contrast to current structural health monitoring systems that use often-cumbersome hardware, incorporating structural health monitoring functionality into one or more ASICs provides a durable yet small, lightweight, low cost, and portable system that can be deployed and operated in field conditions.

Such systems provide significant advantages, especially in applications such as armor structures. Armor structures, such as ceramic plates used in body armor, multi-layer ballistic armors, and other high-strength structures, are difficult to analyze in the field due to the size and weight of current nondestructive evaluation equipment, and due to the advanced materials used. An ASIC-based system is sufficiently small and light to be employed in field conditions, yet is also durable enough to withstand such field conditions.

Such ASIC-based systems are small enough to be deployed on/affixed to the armor itself, or can be a part of a separate portable analysis system.

Figure 1A:
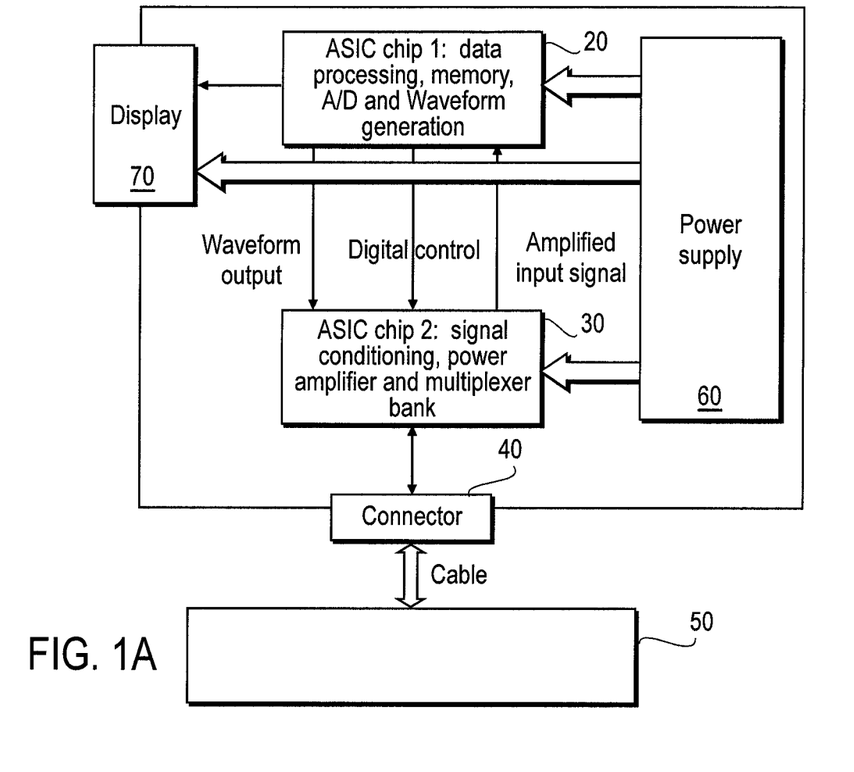
FIG. 1A is a block diagram representation of an application specific integrated circuit (ASIC) based structural health monitoring system in accordance with an embodiment of the invention.

FIG. 1A is a block diagram representation of one such ASIC-based structural health monitoring system in accordance with an embodiment of the invention. System 10 includes a first ASIC 20 and second ASIC 30, a connector 40 connecting the ASICs 20, 30 to sensors/actuators 50, as well as a power supply 60 and display 70. The sensors/actuators 50 are affixed to a structure such as a piece of armor. The remainder of the system 10 can be incorporated into a single unit such as a handheld unit, or any portion thereof can be affixed to the structure. For example, as will be described below, the connector 40 and/or ASICs 20, 30 can be affixed to the structure along with the sensors/actuators 50.

The sensors/actuators 50 can be any set of sensors and/or actuators capable of detecting and transmitting stress waves, respectively. Typically, sensors/actuators 50 include multiple actuating and/or sensing elements placed at discrete locations on the structure, for transmitting stress waves through a structure and detecting resulting waveforms, respectively. As is known, sensors can both passively monitor a structure for stress waves resulting from an impact (whereupon analysis of such stress waveforms can be performed to determine data about any corresponding damage), and monitor the structure for stress waves actively transmitted through the structure by the actuators (whereupon comparison of the resulting waveforms to the original signals transmitted can indicate damage). The invention contemplates use of any sensors and any actuators, affixed to a structure in any manner and any number that allow for evaluation of the structure. However, one suitable sensor/actuator is lead zirconate titanate (PZT) piezoelectric transducers (or any other suitable transducer) that each can act as both a sensor and an actuator. In known manner, each PZT transducer converts electrical signals to stress waves in order to actively query a structure, and converts resulting detected stress waves to electrical signals for analysis.

Figure 1B:
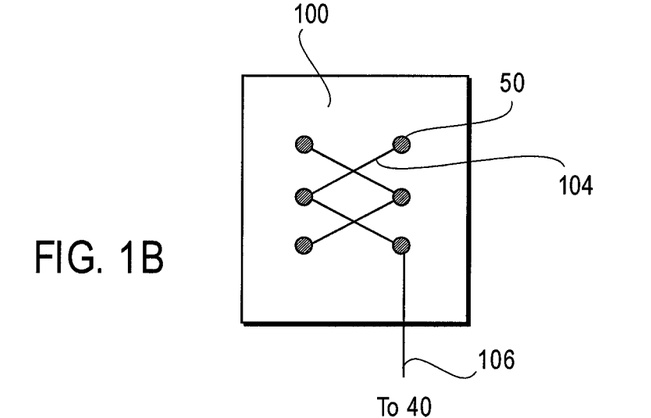
FIG. 1B illustrates an exemplary flexible actuator/sensor layer for use in the system of FIG. 1A.

Furthermore, the sensors/actuators 50 can be individually affixed to a structure, or affixed to a flexible layer that can itself be affixed to a structure. For purposes of illustration, one exemplary sensor system is shown in FIG. 1B, which shows a flexible sensing layer that can be used in accordance with embodiments of the present invention. A diagnostic layer 100 is shown, which contains an array of sensors 50. The sensors 50 can be any sensors, including transducers capable of both generating and receiving signals used in structural health monitoring such as stress waves, and are connected to conductive traces 104. The traces 104 connect (or interconnect, if necessary) sensors 50 to one or more output leads 106 configured for connection to a processor or other device capable of analyzing the data derived from the sensors 50.

The diagnostic layer 100 and its operation are further described in U.S. Pat. No. 6,370,964 to Chang et al., which is hereby incorporated by reference in its entirety and for all purposes. Construction of the diagnostic layer 100 is also explained in U.S. Pat. No. 7,413,919 to Qing et al., which is also incorporated by reference in its entirety and for all purposes. The output leads 106 are electrically connected to connector 40, so that the sensors 50 can be placed in electrical communication with ASIC 30.

The ASICs 20, 30 of system 10 are capable of acting in both "active" and "passive" modes. In active mode, the ASICs 20, 30 generate stress waves from certain actuators and detect those stress waves at sensors in different locations from the actuators. The detected stress waves are examined to determine how they have changed due to propagation through the structure, which can indicate whether they have propagated through a damaged portion of the structure, and how severe that damage is. In passive mode, the ASICs 20, 30 monitor sensors to detect stress waves generated in the structure by impact, operational conditions, or other events. Analysis of these detected stress waves can indicate conditions such as damage, fatigue, and the like.

In particular, ASIC 20 generates waveforms and analyzes detected signals, while ASIC 30 directs the waveforms and detected signals to the correct destination, as well as amplifies and conditions the detected signals. In this embodiment, ASIC 20 generates querying waveforms (i.e. waveforms for generating corresponding stress waves in the structure for use in analyzing the structure to determine its health), and outputs them to ASIC 30 along with control signals directing ASIC 30 to send these waveforms to specific actuators. ASIC 30 then amplifies the querying waveforms and routes the amplified waveforms to those actuators via a multiplexer bank, where they generate corresponding stress waves in the structure that are detected at one or more sensors. The sensors convert these detected stress waves to electrical signals, whereupon ASIC 30 conditions and amplifies the signals, and sends them to ASIC 20 for analysis. ASIC 20 receives and analyzes these signals to determine the health of the structure.

Figure 2:
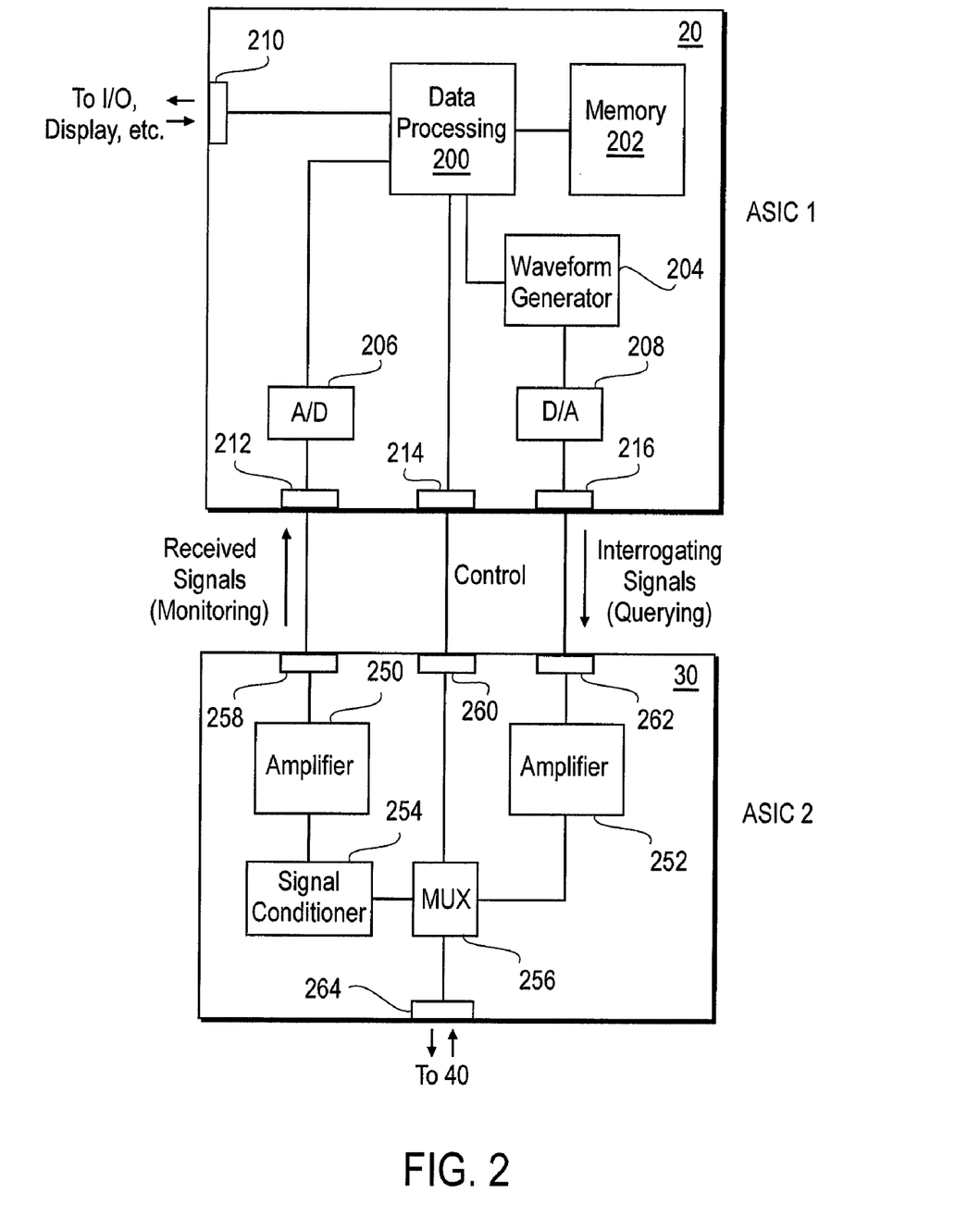
FIG. 2 illustrates further details of the ASICs of FIG. 1A.

FIG. 2 illustrates further details of the ASICs of FIG. 1A. ASIC 20 can include a data processing block 200, memory block 202, waveform generator 204, analog to digital (A/D) converter 206, digital to analog (D/A) converter 208, and interfaces 210-216. The data processing block 200 is a processor such as a central processing unit (CPU) that handles signal generation for active structure querying, and signal analysis for passive monitoring and/or analysis of active signals detected after transmission through the structure. The memory 202 stores information used by data processing block 200, such as digital representations of waveforms used in actively querying the structure, and baseline signal data. The memory 202 can include re-writable memory, so that waveforms and baseline data can be added or updated as desired. A/D converter 206 converts analog signals received from sensors 50 to digital signals for analysis by data processing block 200. Waveform generator 204 generates digital waveforms at the instruction of data processing block 200, and D/A converter 208 converts these digital signals to analog signals for sending to actuators 50.

ASIC 30 can include amplifiers 250, 252, a signal conditioning block 254, a multiplexer (MUX) bank 256, and interfaces 258-264. The amplifiers 250, 252 amplify signals received from sensors 50 and out from the ASIC 20 to the actuators 50, respectively. The MUX bank connects various different actuators/sensors 50 under direction from the data processing block 200, so that signals are transmitted only from specified actuators 50, or so that only specified sensors 50 are monitored.

Figure 3:
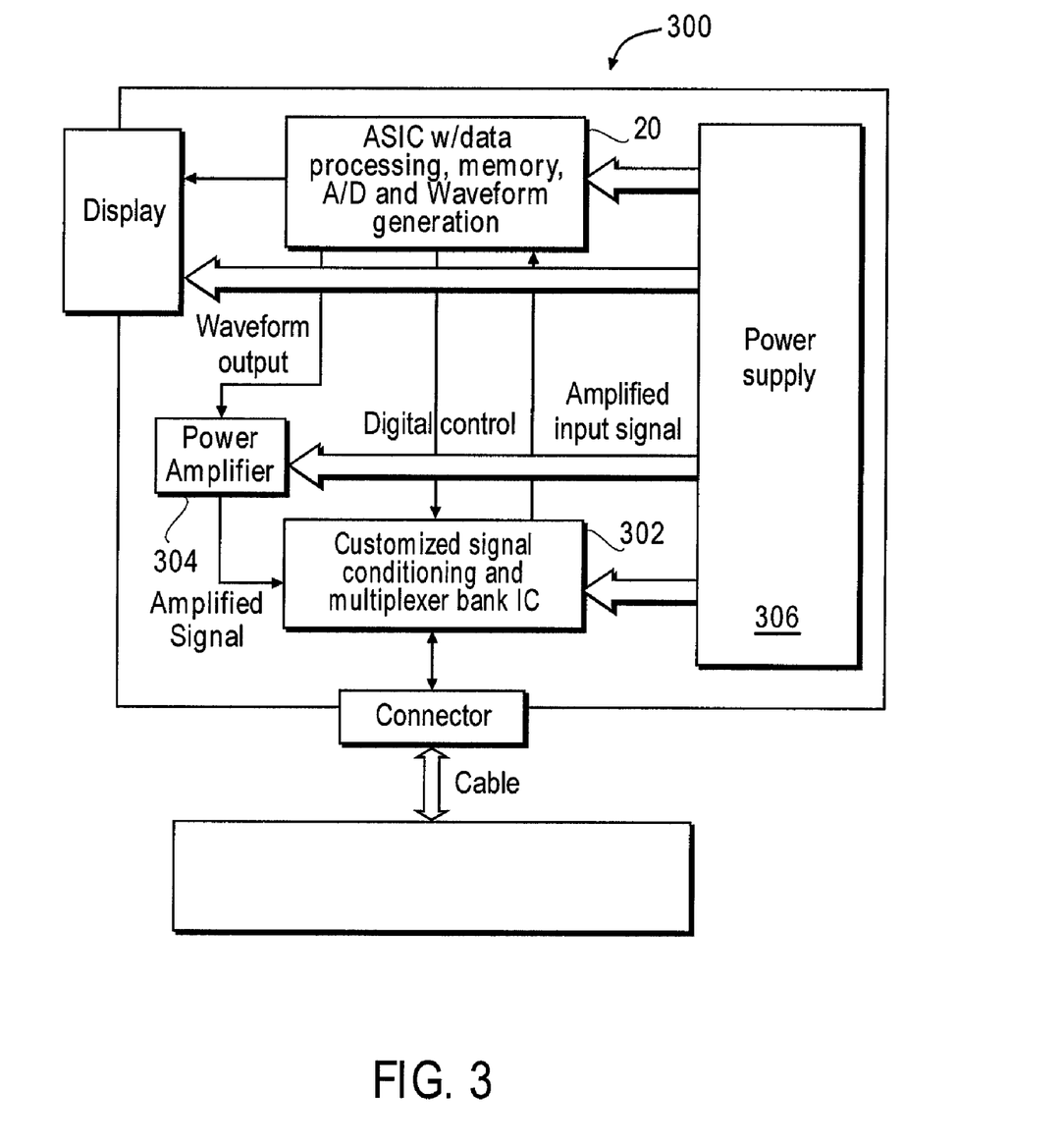
FIG. 3 is a block diagram representation of an ASIC based structural health monitoring system in accordance with a further embodiment of the invention.

It is noted that, in the embodiment of FIG. 1A, power supply 60 is electrically connected to, and supplies power for, display 70 and both ASICs 20, 30. Power supply 60 can be any power supply suitable for providing power to electronic components. However, the invention also encompasses embodiments of system 10 that are structured differently. For example, some applications such as large structures, or thick structures on which sensors are located relatively far from each other, may require higher-voltage actuation signals (signals generated by the ASICs 20, 30 for transmission by actuators 50 through their structure). When the voltages of these actuation signals are sufficiently high, it may be desirable to move amplifier block 250 out from within ASIC 30. This may be done, for example, to avoid problems such as electrical interference with other components of ASIC 30 or overheating/burnout of ASIC 30, and to improve the consistency of ASICs being fabricated. FIG. 3 illustrates one such example. In FIG. 3, structural health monitoring system 300 is constructed similar to system 10 of FIG. 1A. However, ASIC 302, corresponding generally to ASIC 30, does not contain an amplifier 250 integrated within. Rather, a separate, dedicated power amplifier 304 is employed outside of ASIC 302. In this embodiment, power amplifier 304 is located a sufficient distance from the ASICs of system 300 to avoid any problems due to electrical interference or heat. Power supply 306 also supplies power separately to power amplifier 304.

Power supplies 60, 306 can be any power supply suitable for supplying requisite power to ASICs and/or amplifiers. In particular, power supplies 60, 306 can be battery-operated power supplies that contain relatively lightweight batteries for use in portable, in-field applications.

Figure 4:
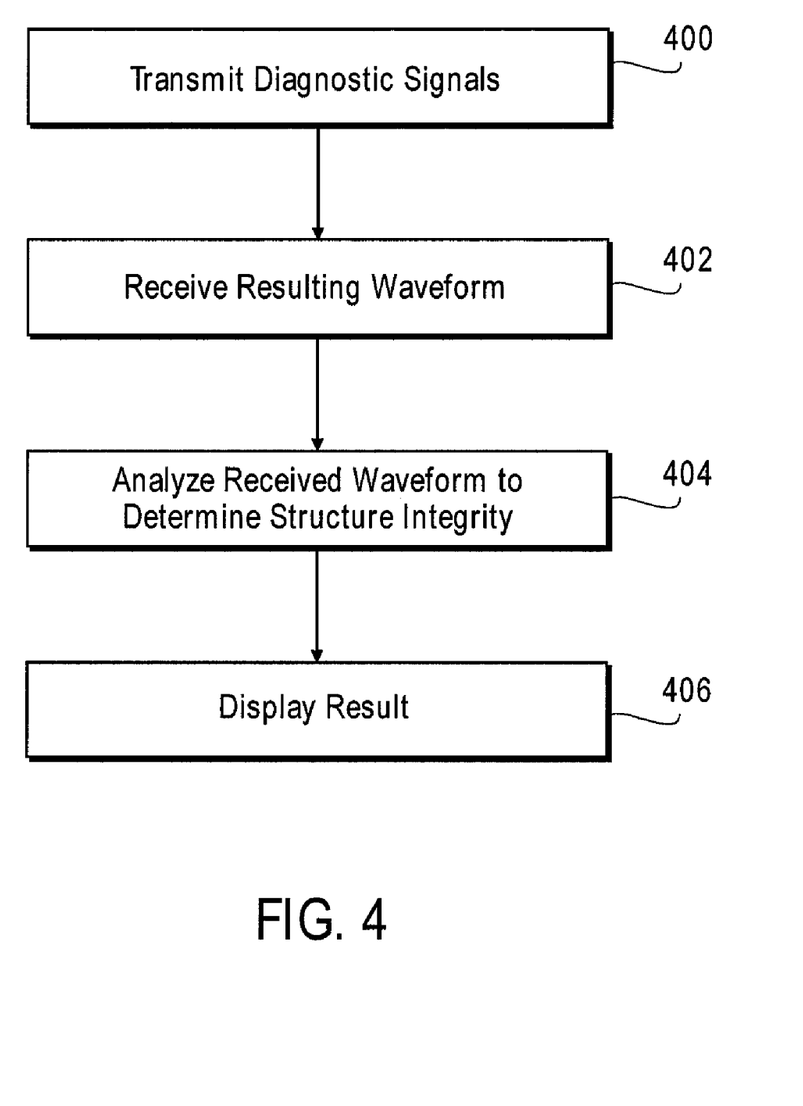
FIG. 4 is a flowchart illustrating one sequence of steps that systems of the invention can perform in order to monitor structural health.

Various hardware configurations of the invention having been described, attention now turns to aspects of their operation. FIG. 4 is a flowchart illustrating one sequence of steps that systems of the invention can perform in order to monitor structural health. As above, systems 10, 300 can be operated in both active and passive modes, where the ASICs 20, 30 and actuators 50 generate stress waves in active mode to actively query the structure, and ASICs 20, 30 and sensors 50 in passive mode simply monitor the structure to detect stress waves generated by impact, structure operation, or the like.

More specifically, FIG. 4 illustrates steps taken in active mode. Here, the ASICs 20, 30 and actuators 50 generate interrogating or querying signals, i.e. stress waves having specified waveforms, that are transmitted through the structure (Step 400). These diagnostic signals propagate through the structure and are received at specified sensors 50 (Step 402), which detect the stress waves and generate corresponding electrical signals. These electrical signals are sent to the ASICs 20, 30 through connector 40, where they are digitized. Processor block 200 then analyzes the digitized waveforms to determine the health or integrity of the structure (Step 404). Results are transmitted to display 70 for viewing by users (Step 406).

Figure 5:
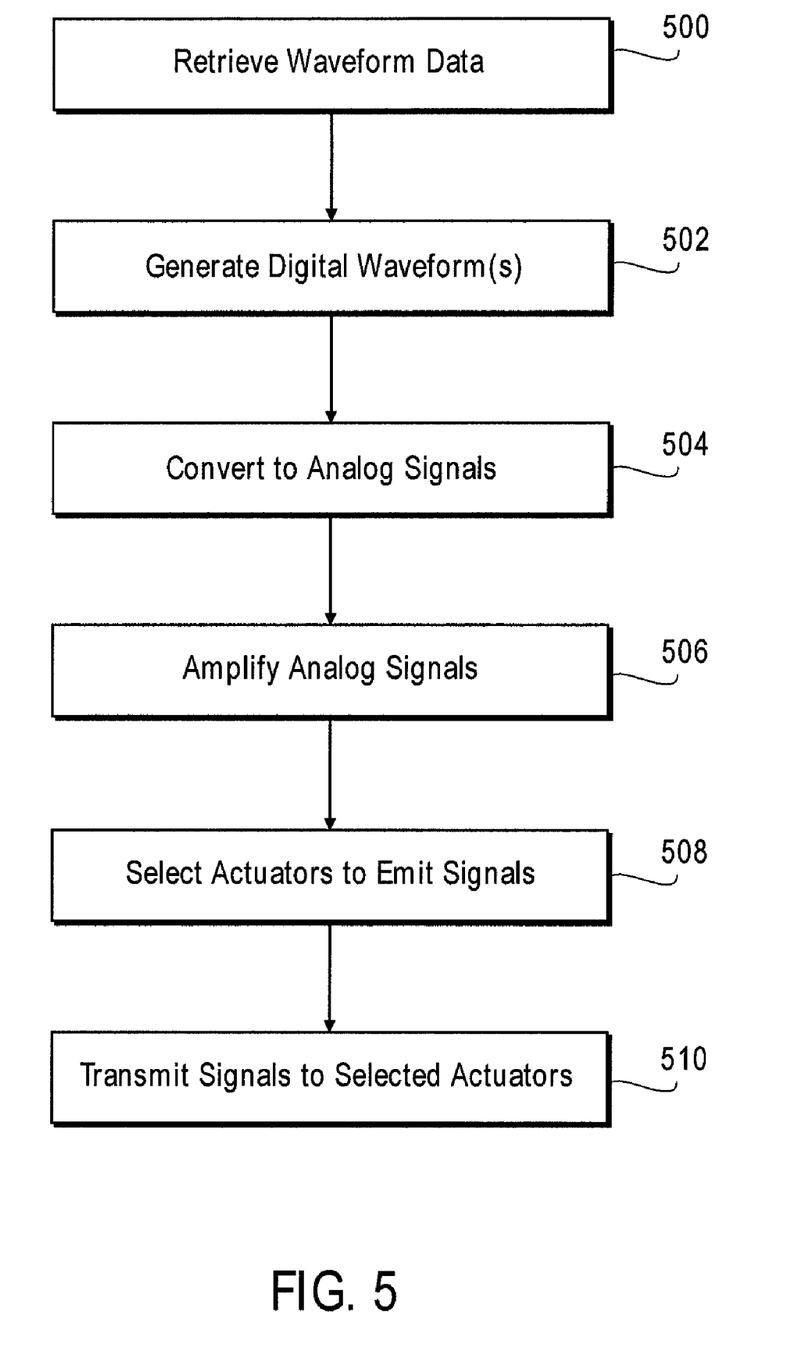
FIG. 5 is a flowchart illustrating further details of signal transmission/structure querying in accordance with embodiments of the invention.
Figure 6:
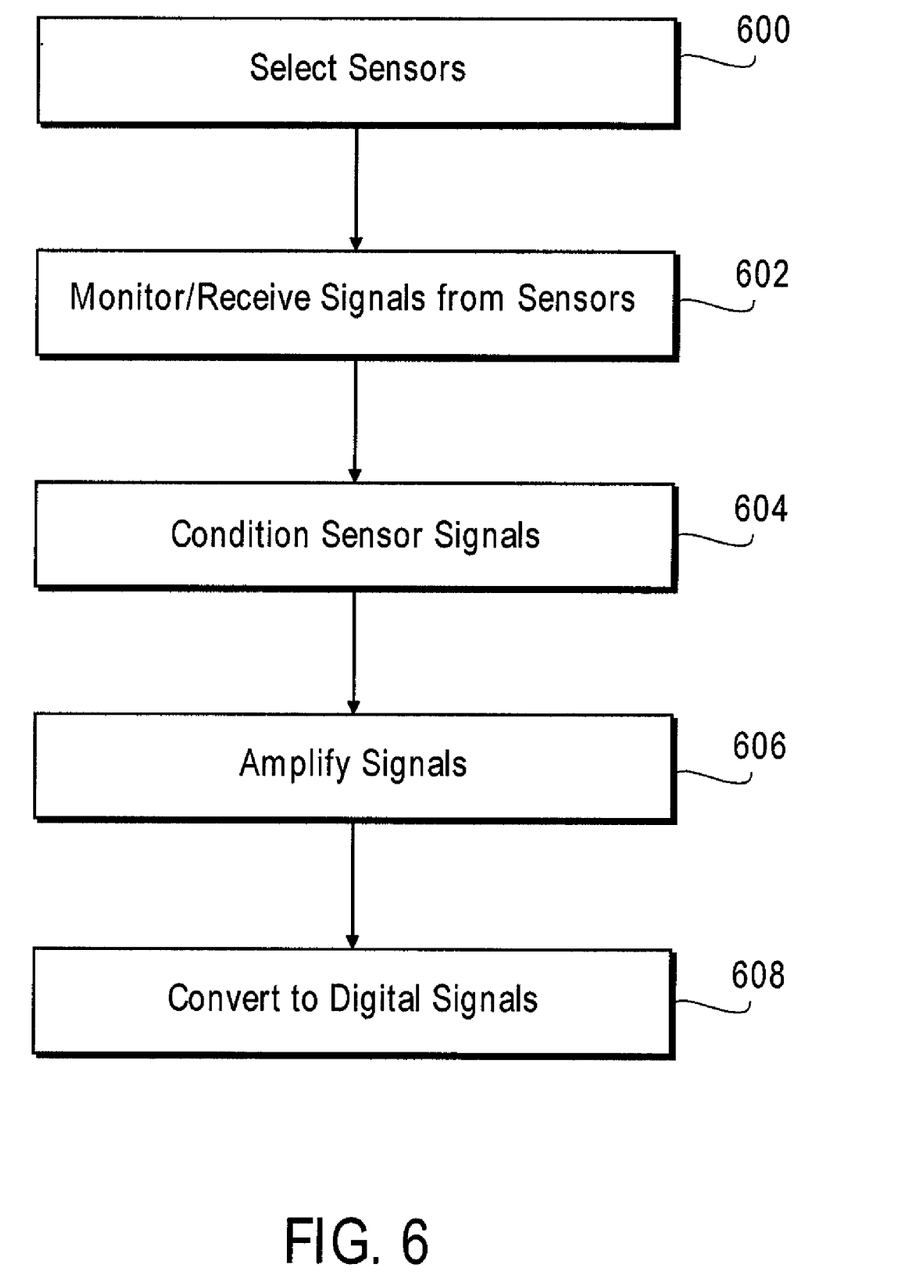
FIG. 6 is a flowchart illustrating further details of signal reception in accordance with embodiments of the invention.
Figure 7:
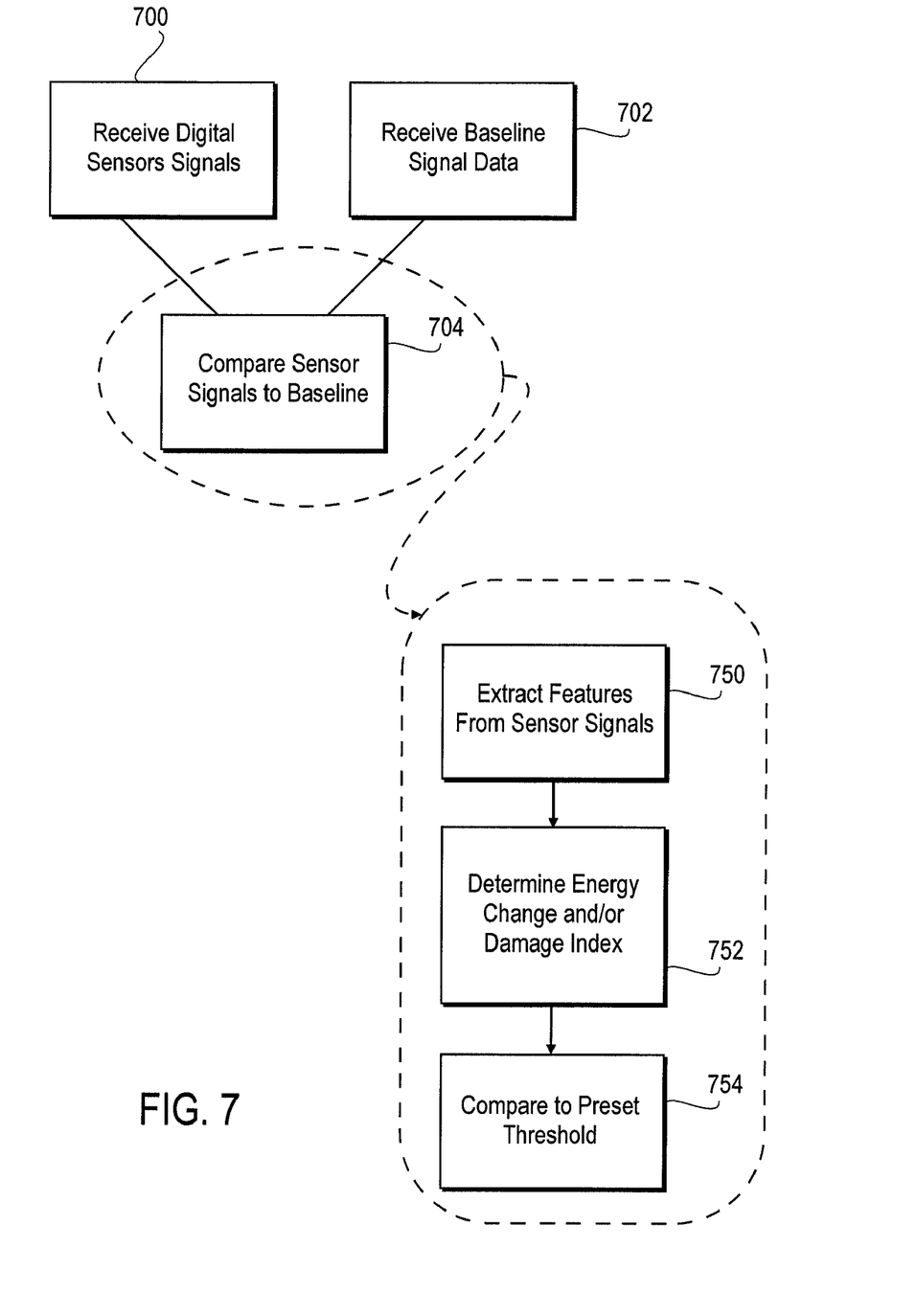
FIG. 7 is a flowchart illustrating further details of signal analysis and health determination in accordance with embodiments of the invention.

FIGS. 5-7 illustrate further details of Steps 400-404. FIG. 5 is a flowchart illustrating further details of Step 400, i.e. the generation and transmission of diagnostic signals in active mode. In summary, ASICs 20, 30 generate a specified electrical waveform and send this waveform to specified actuators 50, which convert this waveform to a stress wave that propagates through the structure. First, processing block 200 retrieves the specified waveform from memory 202 (Step 500), and directs the waveform generator 204 to generate a corresponding digital interrogation waveform, i.e. a time-varying digital signal shaped according to the data retrieved from memory 202 and intended to generate a correspondingly-shaped interrogating stress wave propagating through the structure (Step 502). This digital signal is sent to D/A converter 208, which converts it to an analog signal (Step 504) and sends the analog signal across interfaces 216, 262 to amplifier 252. Amplifier 252 amplifies the analog signal (Step 506) and sends the amplified signal to MUX 256.

The data processing block 200 determines which actuators 50 are to transmit the interrogating waveform into the structure, and sends a command to MUX 256 (via interfaces 214 and 260) directing it to transmit the amplified analog signal to those specified actuators 50 (Step 508). In response, the MUX 256 connects leads 106 from those specified actuators 50 to the output of amplifier 252, whereupon the amplified analog signal is transmitted to those selected actuators 50 (Step 510). The actuators 50 then generate specified stress waves in the structure.

Once these stress waves are generated in the structure, they propagate through it and are received at other sensors 50, as described above in connection with Step 402. FIG. 6 is a flowchart illustrating further details of this Step 402. The processor 200 determines which sensors are to be used to detect the interrogating waveforms, and sends a command to MUX 256 (again, via interfaces 214 and 260) identifying those selected sensors 50 (Step 600). The MUX 256 responds by connecting leads 106 from those specified sensors 50 to signal conditioning block 254, effectively allowing processor 200 to monitor these sensors 50 for any stress waves they detect (Step 602).

Once these selected sensors 50 detect stress waves, whether the result of interrogating signals or any other event, the sensors 50 transmit corresponding analog electrical signals to signal conditioning block 254, which conditions the signals (Step 604). Signal conditioning can include any operations performed on signals input to block 254 to make those signals more readily analyzed by processor 200. These operations can include filtering to remove/attenuate undesired frequencies and/or noise (thus improving signal-to-noise ratio), or other operations. The conditioned sensor signals are then sent to amplifier block 250, where they are amplified for more ready analysis by processor 200 (Step 606). The amplified analog signals are sent to A/D converter 206 of ASIC 20 via interfaces 258 and 212, where they are converted to digital signals (Step 608) and sent to processor 200.

As above, the processor 200 commences with Step 404 once it receives these signals. FIG. 7 is a flowchart illustrating further details of signal analysis and health determination taken by processor 200 in connection with Step 404. More specifically, the processor 200 receives these digital signal representations (Step 700), and retrieves baseline signal data from memory 200 (Step 702). This baseline signal data is known, and typically is the stored representation of the waveform received from the same sensor 50 that transmitted the signal received at Step 700, using the same interrogating waveform and sent from the same actuator 50 at some previous "baseline" structure state. The baseline signal data thus typically describes the "baseline" state of the structure along that particular actuator/sensor path. Any changes to the structure along this path are thus typically reflected in the signal received by the processor 200 at Step 700. Accordingly, the signal received at Step 700 is compared to this retrieved baseline signal (Step 704), whereupon such a comparison can indicate changes from the baseline signal to the currently-received signal, thus indicating a change in the structure from its baseline state to its current state.

The comparison of Step 704 can be carried out in any manner. As one example, features such as the signal magnitude envelope, phase difference between the received signal and baseline signal, peak amplitudes, total signal energy within a certain time window, frequency spectra, or the like can be extracted by processor 200 (Step 750), and used to determine signal changes, a relevant damage index, or any other desired quantity (Step 752). These quantities can then be compared to preset thresholds (Step 754), which can indicate damage or another relevant change in the structure if these thresholds are exceeded.

While FIGS. 5-7 illustrate further details of the steps taken in connection with FIG. 4, one of ordinary skill in the art will observe that the invention is not limited to the steps of FIGS. 5-7. Rather, the invention encompasses operation of ASICs 20, 30 in any manner consistent with determination of the health of the structure being monitored. For example, while FIG. 4 illustrates steps taken in active mode, the invention encompasses use of systems 10, 300 in passive mode as well. It is thus possible to utilize systems 10, 300 to monitor structures without actively transmitting interrogating signals through it. In this manner, systems 10, 300 can employ the steps of FIG. 6, without those of FIG. 5, to monitor specified sensors 50 for any stress waves detected in the structure. In strictly passive monitoring, no relevant baseline signal would typically exist. Accordingly, embodiments of systems 10, 300 employing such passive monitoring can then determine structure health by comparing the received signals from the sensors 50 against certain predetermined criteria. For instance, quantities such as peak amplitude and dominant signal frequencies can indicate the occurrence an impact and its severity, while the times at which peak signal amplitudes are received at various sensors 50 can be used to triangulate the location of the impact.

It should be noted that the invention encompasses use of systems 10, 300 on any type of structure to which sensors/actuators 50 can be affixed. As above, this allows the systems of the invention to provide a lightweight and portable, yet durable, structural health monitoring system that can be used in many different environments, and that is suitable for many different applications. One such application is the monitoring and/or analysis of armor structures such as ballistic protective body armor. Advanced materials and configurations for such body armor often render other nondestructive evaluation techniques ineffective in detecting damage in modem body armor. Additionally, it is often desirable to quickly scan body armor in field conditions, to make a rapid decision as to whether to replace a combatant's body armor. Systems of the invention that employ ASICs such as ASICs 20, 30 are thus superior to many other nondestructive evaluation systems, in that they can be utilized to detect damage in modem body armor, yet also are durable and lightweight, allowing for use in field conditions. Systems of various embodiments of the invention are thus well suited for use in conjunction with body armor, especially in field conditions.

It is also noted that systems of the invention can be utilized with body armor in different ways. For example, various components of systems 10, 300 can be placed on the body armor itself ("on-board"), or located remote therefrom ("off-board"). Additionally, the sensors/actuators 50 used in conjunction with systems 10, 300 can be affixed to the surface of body armor or embedded within, and can be placed on a flexible substrate or be separately attached to the armor.

Figure 8A:
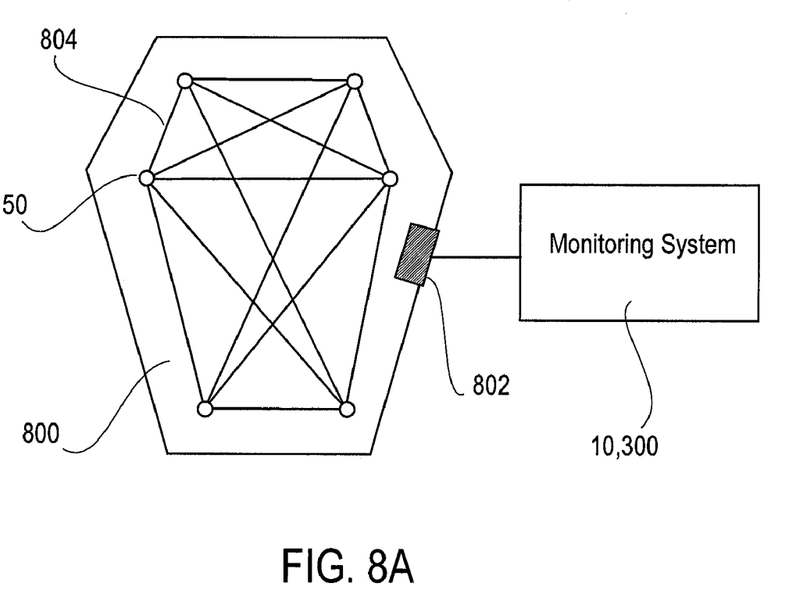
FIG. 8A is a block diagram representation of an armor structure with an off-board ASIC based structural health monitoring system.

FIG. 8A is a block diagram representation of an armor structure with an off-board ASIC based structural health monitoring system. Here, a piece of body armor 800 has a number of sensors/actuators 50 affixed thereto and spatially distributed thereon. As in FIG. 1B, the sensors/actuators 50 have electrical leads (not shown) extending to interface 802, which can be any electrical interface. Signal paths 804 exist between each pair of sensors/actuators 50, some of which are shown. As signals can travel along each path from actuator to sensor, each signal path represents a path along which the health of the structure 800 can be monitored. The interface 802 is electrically connected to a monitoring system of the invention, such as system 10 or system 300. That is, the interface 802 can be electrically connected to connector 40, so that signals can be sent to/from the actuators/sensors 50.

The monitoring system 10, 300 can be operated as described above, with monitoring system 10, 300 sending electrical waveforms through interface 802 to specified ones of the actuators 50 so as to generate stress waves along desired signal paths 804. These stress waves are detected by sensors 50 at the ends of these specified paths 804, where the sensors 50 generate corresponding electrical waveforms and send them back to system 10, 300. Changes from a stored baseline waveform to the waveform received by system 10, 300 can indicate changes in the state of the structure 800 along those paths 804.

Figure 8B:
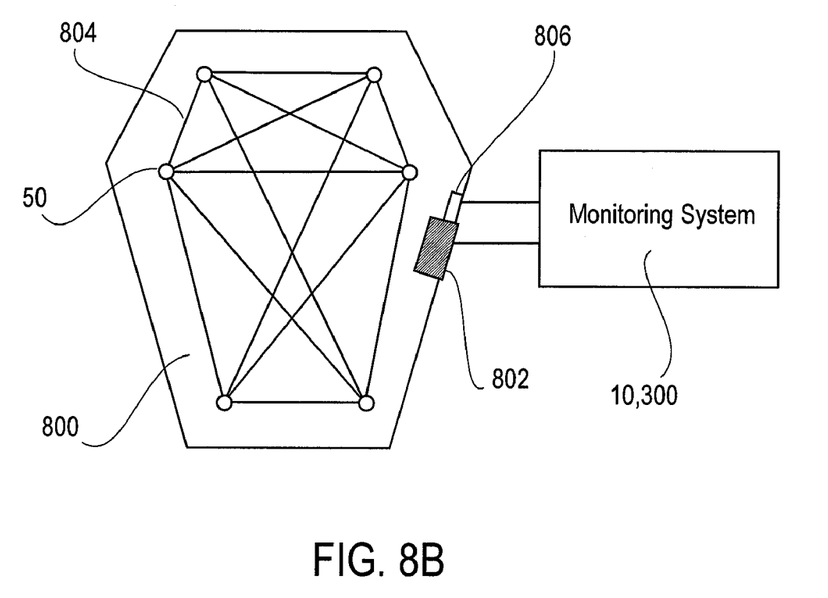
FIG. 8B is a block diagram representation of an armor structure with on-board data storage and off-board ASIC based structural health monitoring system.

The invention also includes embodiments in which any one or more components of systems 10, 300 can be located on-board the armor, i.e., affixed to the armor 800 along with sensors/actuators 50. As one example, FIG. 8B is a block diagram representation of an armor structure with on-board data storage and off-board ASIC based structural health monitoring system. Here, the memory 202 is moved from within system 10 to the armor 800 itself, affixed to the armor as a memory module 806. In some embodiments, module 806 is preferably a solid state memory package or chip that is placed in a protective housing. Embodiments can also include a chip package that is removable so that the memory can be upgraded or replaced, or its contents changed, relatively easily. In the embodiments of FIG. 8B, the memory module 806 remains electronically connected to system 10, 300 as shown, so that processor 200 can still retrieve or store information as necessary.

Figure 9:
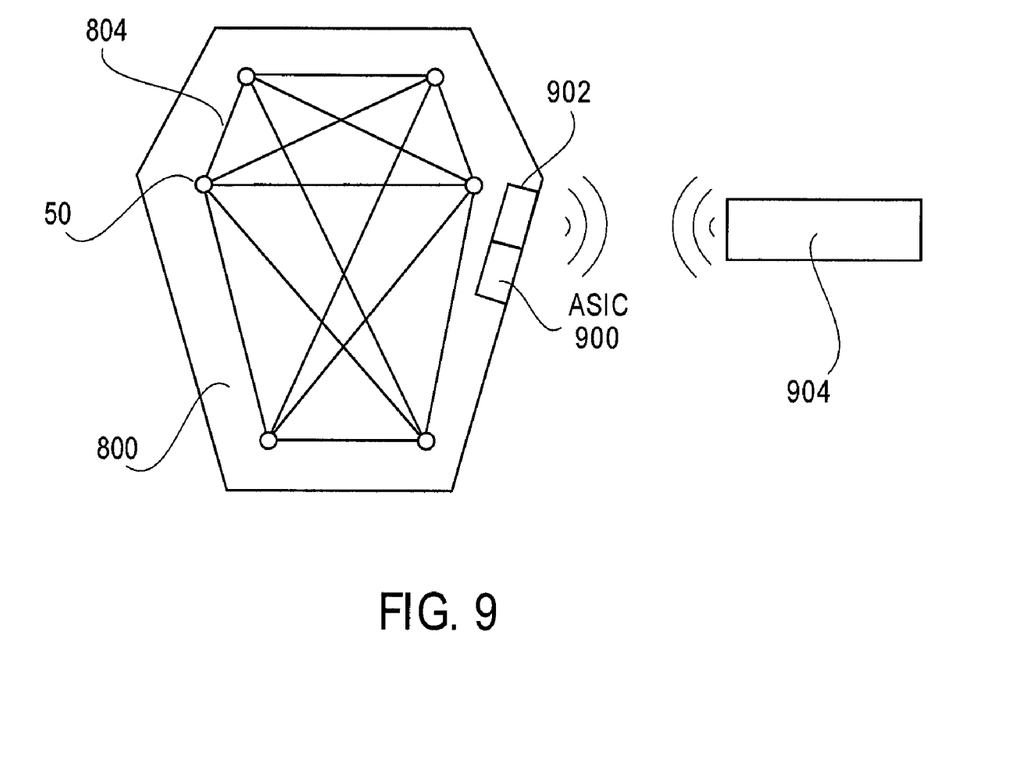
FIG. 9 is a block diagram representation of an armor structure with an on-board ASIC based structural health monitoring system.

As another example, FIG. 9 is a block diagram representation of an armor structure with ASIC module 900 located on-board the armor structure 800. Here, ASIC module 900 is coupled to the structure 800. Module 900 can include any one or more of ASICs 20 and 30, any other structures utilized in their operation, and a protective housing. In particular, it may be preferable to locate both ASICs 20, 30 on-board, as well as their power supplies 60, 306.

Here, the ASICs 20, 30 of module 900 communicate with a control station 904 via a wireless transceiver 902. The control station 904 can be any device for directing any operations of the ASICs 20, 30 and/or receiving any resulting data. For example, the control station 904 can simply be a display, or it can be a portable computational device such as a hand-held analysis unit capable of directing the ASICs 20, 30 to initiate a scan (i.e., an interrogation) of the structure and displaying resulting data such as an indication of any damage the armor has sustained. In this manner, the embodiment of FIG. 9 yields a compact, lightweight and portable system capable of determining the health of armor relatively quickly, and in field conditions. It should also be noted that, while FIG. 9 illustrates a wireless connection between module 900 and control station 904, embodiments of the invention can utilize any connection between any components. For example, connections between any components located on the structure and any other elements of monitoring systems 10, 300 can be wired or wireless. Similarly, a wired or wireless connection can exist between the monitoring systems 10, 300 and any control station 904 that may be present. Any ASICs or other structures not located on armor 800 can be positioned remotely, such as in control station 904.

Figure 10:
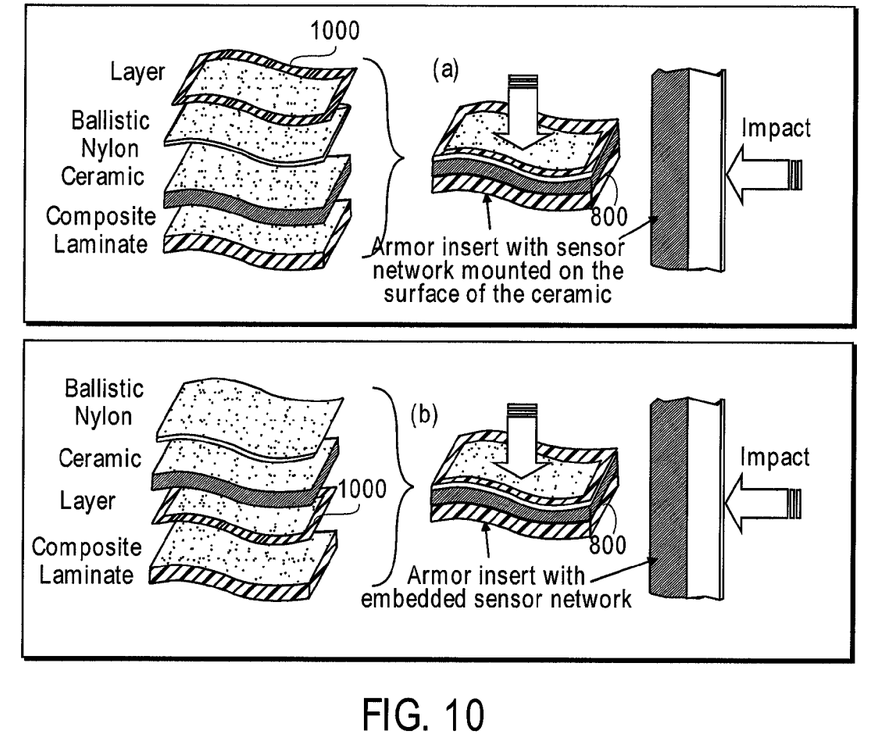
FIG. 10 illustrates further details of construction and composition of armor structures.
Figure 11:
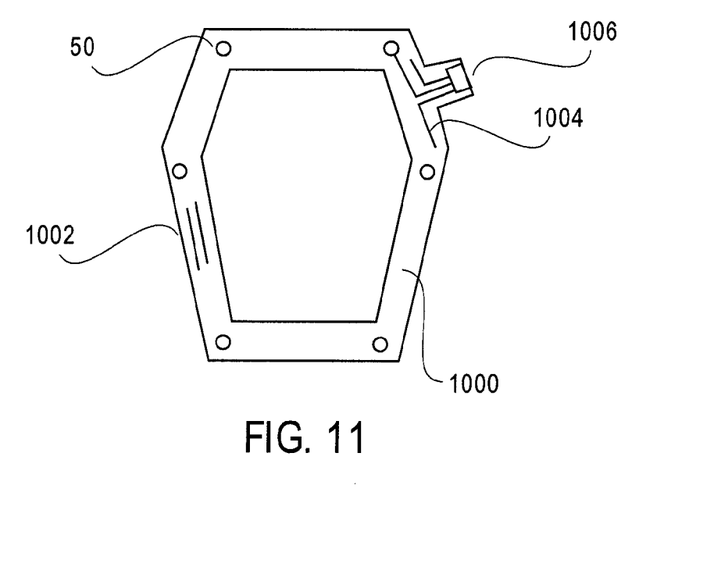
FIG. 11 illustrates further details of armor structures for use with off-board ASIC based structural health monitoring systems.

As noted previously, the invention includes embodiments in which the sensors/actuators 50 are placed individually on structures such as armor 800, and embodiments in which the sensors/actuators 50 are first placed on a flexible substrate, and the substrate is either affixed to or embedded within the structure. FIGS. 10 and 11 illustrate further details of this latter configuration. More specifically, sensors 50 are affixed to flexible substrate 1000. Substrate 1000 also supports leads 1002 that electrically connect/interconnect sensors/actuators 50 as desired, and wires 1004 that connect sensors/actuators 50 to interface 1006, to place sensors/actuators 50 in electrical communication with the remainder of systems 10, 300. The substrate 1000 can be shaped to fit the structure as desired. Here, for example, the substrate 1000 is shaped to fit armor 800, so that it both fits within the spatial confines of the armor 800 and generally conforms to its surface(s).

The substrate 1000 can be either affixed to an outer surface of armor 800, or can be incorporated within. In particular, the substrate 1000 can be embedded within modern multi-layer composite armor by incorporating it within layers during the armor's fabrication process. FIG. 10 illustrates examples of both configurations. In particular, the upper configuration of FIG. 10 shows an armor structure 800 made partly of a composite laminate, ceramic plate, and ballistic nylon covering its outer surface, followed by sensor/actuator layer 1000. Similarly, the lower configuration of FIG. 10 shows an armor structure 800 in which the sensor/actuator layer 1000 is sandwiched between the composite laminate and the ceramic plate, so that the sensor/actuator layer 1000 is embedded within layers of the armor structure 800 itself.

Embodiments of the invention having been described, one of ordinary skill in the art will observe that the above-described components, as well as their connections, attachments, and fabrication, can be implemented in any manner. For example, the blocks of FIG. 2 can be implemented as using known digital components and solid state devices, fabricated according to known methods. The electrical connections between sensors/actuators 50 and systems 10, 300 can be standard wires, electrical traces, or the like. Additionally, protective modules employed to protect components of the invention such as ASICs can be any known modules used to house and protect solid state electronics or associated components. Also, components such as the above-described MUXes can be any known multiplexing device or set of switches operable to direct signals to/from sensors/actuators 50, and separate MUX banks can be implemented for actuators and sensors if desired. It is also noted that the solid-state components of embodiments of the invention can be packaged in any appropriate manner. For instance, ASICs 20 and 30 can be implemented on the same silicon and packaged in a single chip package, or can be implemented and packaged as separate chips. Indeed, the entire system (minus display) 10, 300 can be packaged as a single integrated chip, or any one or more components can be packaged separately.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description. They are not intended to be exhaustive or to limit the invention to the precise forms disclosed. Many modifications and variations are possible in view of the above teachings. For example, any one or more of the ASICs of the invention, or their associated components such as power supplies, interfaces, transceivers or the like, can be located on-board or off-board the structure they monitor. Additionally, the sensors/actuators 50 can be any sensors, any actuators, or any transducers capable of acting as both sensor and actuator. These sensors/actuators can be located on a flexible substrate or individually placed, and they (along with their substrate, if one is employed) can be affixed to an outer surface of a structure or embedded within. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A structural health monitoring system, comprising:
a structure; and
at least one integrated circuit, the at least one integrated circuit configured to transmit interrogating signals to a plurality of actuators coupled to the structure, to receive sensor signals from a plurality of sensors coupled to the structure, and to determine a health of the structure according to a comparison of the received sensor signals to baseline signals;
wherein the interrogating signals correspond to stress waves propagated through the structure so as to query the structure;
wherein the sensor signals correspond to stress waves detected by the plurality of sensors;
wherein the baseline signals correspond to a baseline state of the structure;
wherein one or more integrated circuits of the at least one integrated circuit is coupled to the structure, and
wherein the at least one integrated circuit includes a first integrated circuit comprising:
at least one memory storing baseline signal data corresponding to the baseline signals, and interrogating signal data corresponding to the interrogating signals; and
a processing block configured to receive sensor signals and programmed to retrieve the baseline signal data, to compare the sensor signals to the baseline signals according to the retrieved baseline signal data, to output results data resulting from the compare, and to initiate transmission of the interrogating signals for querying the structure.

2. The structural health monitoring system of claim 1, wherein the plurality of actuators and the plurality of sensors both comprise piezoelectric transducers.

3. The structural health monitoring system of claim 1, wherein the structure is a ballistic protective armor.

4. The structural health monitoring system of claim 1, wherein the at least one integrated circuit further comprises:
a second integrated circuit in electronic communication with the first integrated circuit, the second integrated circuit comprising:
a signal conditioning block for conditioning the sensor signals, the signal conditioning block being configured to transmit the conditioned sensor signals to the processing block of the first integrated circuit.

5. The structural health monitoring system of claim 4, further comprising a power supply in electrical communication with the first and second integrated circuits, the power supply configured to supply power to both the first and second integrated circuits.

6. The structural health monitoring system of claim 4,
wherein the sensor signals received by the first integrated circuit are analog sensor signals;
wherein the first integrated circuit further comprises an analog to digital (A/D) converter connected to the processing block, the A/D converter configured to convert the analog sensor signals to digital sensor signals; and
wherein the processing block is further programmed to compare the digital sensor signals to the baseline signals.

7. The structural health monitoring system of claim 4,
wherein the first integrated circuit further comprises:
a signal generator receiving the interrogating signal data and generating digital interrogation signals therefrom; and a digital to analog (D/A) converter in electronic communication with the signal generator, the D/A converter configured to convert the digital interrogation signals to the interrogating signals, wherein the interrogating signals are analog signals.

8. The structural health monitoring system of claim 4, wherein the processing block is further programmed to write the results data to the at least one memory.

9. The structural health monitoring system of claim 4, wherein the first integrated circuit is packaged with the second integrated circuit.

10. The structural health monitoring system of claim 4, wherein the second integrated circuit further comprises an amplifier configured to amplify the interrogating signals.

11. The structural health monitoring system of claim 4, further comprising an amplifier in electrical communication with the first and second integrated circuits, the amplifier configured to receive the interrogating signals from the first integrated circuit, to amplify the interrogating signals, and to transmit the amplified interrogating signals to the second integrated circuit.

12. The structural health monitoring system of claim 11, further comprising a power supply in electrical communication with the first and second integrated circuits and the amplifier, the power supply configured to supply power to the amplifier and to both the first and second integrated circuits.

13. The structural health monitoring system of claim 4, wherein the processing block is further programmed to transmit an actuator selection signal selecting one or more actuators for receiving the interrogating signals; and wherein the second integrated circuit further comprises a first multiplexer block configured to receive the actuator selection signal and to route the interrogating signals to the selected one or more actuators accordingly.

14. The structural health monitoring system of claim 13, wherein the processing block is further programmed to transmit a sensor selection signal selecting one or more of the sensors for monitoring; and wherein the second integrated circuit further comprises a second multiplexer block configured to receive the sensor selection signal and to route the first signals from the selected one or more of the sensors to the signal conditioning block.

15. The structural health monitoring system of claim 4, wherein at least one of the first integrated circuit and the second integrated circuit is placed remote from the structure.

16. The structural health monitoring system of claim 4, wherein at least one of the first integrated circuit and the second integrated circuit is coupled to the structure.

\* \* \* \* \*